United States Patent [19]

Marko et al.

[11] Patent Number: 5,000,934

[45] Date of Patent: Mar. 19, 1991

[54] METHOD FOR QUENCHING SILICON SPENT BED

[75] Inventors: Ollie William Marko, Carrollton; Panela Sue Borah, Louisville, both of Ky.

[73] Assignee: Dow Corning Corporation, Midland, Mich.

[21] Appl. No.: 434,154

[22] Filed: Nov. 13, 1989

[51] Int. Cl.$^5$ .......................... C01B 33/12; C07F 7/04
[52] U.S. Cl. ..................................... 423/335; 423/659; 423/DIG. 20; 556/465
[58] Field of Search ................. 423/335, 659, DIG. 6, 423/DIG. 20; 556/465

[56] References Cited

U.S. PATENT DOCUMENTS

| | | | |
|---|---|---|---|
| 4,690,810 | 9/1987 | Breneman et al. | 423/335 |
| 4,824,652 | 4/1989 | Hosokawa | 423/348 |

*Primary Examiner*—Gary P. Straub
*Assistant Examiner*—Timothy C. Vanoy
*Attorney, Agent, or Firm*—William F. Boley

[57] ABSTRACT

The instant invention is a method for the quenching of a spent bed resulting from the reaction of organic halides with silicon metal to form organohalosilanes. The method employs a strong base and elevated temperature to digest the hydrophobic siloxane-rich coating and dislodge the carbon coating which forms around the spent bed particles. Removal of these coatings allows more rapid and complete quenching of the autoxidants on the surface of the spent bed particles.

9 Claims, No Drawings

METHOD FOR QUENCHING SILICON SPENT BED

BACKGROUND OF THE INVENTION

This invention relates to a method for the quenching of the spent bed resulting from the reaction of organic halides with silicon metal to form organohalosilanes. It is well known in the art that the sPent bed resulting from the reaction of organic halides with silicon metal is highly susceptible to atmospheric oxidation, and in an unquenched state can represent a serious potential fire hazard.

It is postulated that such fires result from the autoxidation of silicon hydride (SiH) and polysilane (SiSi) moities present in the spent bed. These oxidative processes may be represented by the following chemical reactions:

$$2 \text{ SiSi} + O_2 \rightarrow 2 \text{ SiOSi}$$

$$2 \text{ SiH} + O_2 \rightarrow 2 \text{ SiOH}$$

It is known that the oxidizable SiSi and the SiH moities may be destroyed by reaction with water, catalyzed by either strong acids or bases. Eaborn, C., Organosilicon Compounds, Butterworths Scientific Publications, London, 1960, p. 200 and p. 354. These reactions are:

$$\text{SiSi} + 2 H_2O \rightarrow 2 \text{ SiOH} + H_2$$

$$\text{SiH} + H_2O \rightarrow \text{SiOH} + H_2$$

However, neither autoxidant is readily attacked by water, nor by bases as weak as sodium bicarbonate (pH 8.4). These reactions proceed with great difficulty because of the tendency to form a siloxane-rich hydrophobic shell around the spent bed particles hindering the reaction. The siloxanes are formed as the result of residual chlorosilanes in the spent bed:

$$\text{SiCl} + H_2O \rightarrow \text{SiOH} + HCl$$

$$2 \text{ SiOH} \rightarrow \text{SiOSi} + H_2O$$

In addition to this siloxane-rich hydrophobic shell, the inventors have found, that in the case of spent beds from the reaction of organic halides with silicon, an inert carbon containing shell is also formed around the spend bed silicon particles. These two types of shells are believed by the inventors to be the principle hindrance to effective quenching of spent beds resulting from the reaction of organic halides with silicon.

Breneman, et al., U.S. Pat. No. 4,690,810, issued Sept. 1, 1987, discloses the use of lime to convert a liquid chlorosilane mixture contaminated with various metal chlorides and minor amounts of metals into environmentally acceptable products. No mention is made of quenching a spent bed resulting from the reaction of silicon metal with an organic halide.

Hosokawa, U.S. Pat. No. 4,724,122, issued Feb. 9, 1988, discloses a method for treating the reaction residue from the preparation of organochlorosilanes or chlorosilanes by the reaction of silicon metal with a chlorinated hydrocarbon. The disclosed method consisted of combining the reaction residue with water and granulating the residue. The granulated residue (spent bed) was then coated with an inert organic powder.

BRIEF SUMMARY OF THE INVENTION

The instant invention is a method for the quenching of a spent bed resulting from the reaction of organic halides with silicon metal to form organohalosilanes. The method employs a strong base and elevated temperature to digest the hydrophobic siloxane-rich coating and dislodge the carbon coating which forms around the spent bed particles. Removal of these coatings allows more rapid and complete quenching of the autoxidants on the surface of the spent bed particles.

DESCRIPTION OF INVENTION

The instant invention is a method for more quickly and thoroughly quenching the spent bed that results from the reaction of metallic silicon with an organic halide. The method described reduces the possibility of spontaneous combustion caused by autoxidation of materials within the spent bed. The described method comprises the following steps:

(A) forming an aqueous basic solution;
(B) heating the aqueous basic solution to a temperature of about 50° C. to 100° C.;
(C) combining the spent bed with the heated aqueous basic solution to form a suspension;
(D) stirring the suspension to effect quenching of the spent bed; and
(E) separating the quenched spent bed from the heated aqueous basic solution.

The term spent bed refers to reduced activity residual silicon resulting from the reaction of an organic halide with silicon metal. In addition to silicon, the spent bed may also include amounts of process catalyst, unreacted organic halide, carbon residues, impurities present in feed materials and products of the reaction.

The inventors have found the spent bed resulting from the reaction of an organic halide with silicon to be particularly difficult to quench by standard techniques. The inventors theorize that this difficulty in quenching is the result of, first, a hydrophobic siloxane-rich shell which forms around the silicon particles of the spent bed. Second, the inventors have found that decomposition products of the organic halides form a carbon containing layer on the silicon particles. The inert nature of the carbon layer further serves to hinder contact of the autoxidants with water. Also, the carbon layer serves as a relatively low igniting fuel source, thus propagating fires resulting from spontaneous combustion. The inventors believe that the method of the instant invention acts to digest and dislodge the hydrophobic siloxane-rich and carbon layers from the particles, making quenching of the spent bed more rapid and complete.

The organic substituent of the organic halide may be, for example, methyl, ethyl, or phenyl. The halide present in the spent bed may be chloride, iodide, fluoride, or bromide. The organic halide can be, for example, methyl chloride.

The process consists of forming an aqueous basic solution. The pH of the aqueous basic solution can be between pH 10 to pH 14. Preferred is an aqueous basic solution of pH 12 to pH 14. The aqueous basic solution can be formed from any inorganic basic material whose disassociation results in an aqueous solution of pH 10 to pH 14. For example inorganic basic materials such as CaO, KOH Ca(OH)$_2$, Na$_2$CO$_3$, NaOH, and Mg(OH)$_2$.

The required concentration of the inorganic basic material in aqueous solution will depend upon the particular spent bed to be neutralized. The basic material may be totally or partially soluble in the aqueous solution. Dissolution may occur as the cation is consumed in the quenching process. To assure as complete as possible neutralization of the halogen present in the spent bed, the cation of the base should be present in at least stoichiometric equivalence. It is preferred that the cation of the base be in 10 to 100% stoichiometric excess to the halogen in the spent bed. The presence of excess cation allows for loss of cation, while still assuring good neutralization of the spent bed. For example, when using lime, CaO, to neutralize a methyl chloride spent bed, a 5 to 10 weight percent of lime to spent bed has been shown to be effective.

The aqueous basic solution is heated to a temperature between about 50° C. and 100° C. A preferred temperature range is about 50° C. to 70° C. Temperatures below about 50° C. may be used in this process, but this will extend the time required to quench the spent bed. The upper temperature limit of 100° C., the boiling point of water, could be exceeded to kinetic advantage, but would require the use of pressurized equipment. The aqueous basic solution can be heated to the desired temperature by standard means, for example, steam lance, heating jacket, and the heat of reaction.

The spent bed is combined with the heated aqueous basic solution to form a suspension. The spent bed can be added to the heated aqueous basic solution as a single volume, by slow continuous addition, or by sized portions. It is preferred that about a 5:1 ratio, weight/weight, of the basic solution to the spent bed be maintained. The importance of this ratio is in providing a heat sink for the reaction and allowing for agitation to keep the spent bed in suspension. In practice a ratio of about 2:1 to 10:1 may be employed. The upper limit is chiefly determined by the capability of the equipment used, while the lower limit is determined chiefly by the consideration of maintaining a suspension.

The suspension of the spent bed in the basic solution is maintained for a period of time adequate to quench the spent bed. In general, the time required to quench the spent bed is dependent upon the source of the spent bed, the pH of the basic solution, and the temperature. The inventors believe that the strong base acts to digest the siloxane-rich and carbon coatings from around the spent bed particles, allowing quicker and more complete neutralization of the spent bed. An indication of the effectiveness of the instant invention is a shortening of the time before a significant exothermic reaction occurs in the suspension. In practice, the temperature of the process can be monitored to determine the occurrence of this exothermic reaction and its subsequent subsidence to safe levels. A preferred time for stirring the suspension to effect quenching of the spent bed is about 6 to 12 hours under preferred temperature and time conditions. However, monitoring of the temperature of the spent bed may indicate shorter time periods to be effective. The quenched spent bed is separated from the heated aqueous basic solution by any conventional equipment for separating suspended solids from liquids, for example, a filter press.

So that those skilled in the art may better understand and appreciate the instant invention, the following examples are presented. These examples are presented to be illustrative and are not be construed as limiting the claims as delineated herein.

EXAMPLE 1:

Preliminary studies indicated it is difficult to duplicate spontaneous combustion with laboratory size samples of spent bed. This appeared to be due to the lack of thermal insulating capability of the small samples. However, it was found that the relative thermal activity of small samples could be ascertained by placing the samples directly on the surface of a hotplate maintained at a temperature of about 390° C. Unquenched spent bed immediately caught fire when placed onto the hotplate with the fire propagating throughout the sample.

By comparison, a spent bed sample quenched by an embodiment of the instant invention did not catch fire. The test sample was quenched using a one liter resin lined kettle fitted with a thermometer, teflon bladed stirrer and air motor, water condenser, and solids addition port. Approximately 500 g of an aqueous 5 percent calcium oxide slurry was added to the kettle and heated to 70° C. With vigorous stirring, 100 g of spent bed from the reaction of methylchloride with silicon metal was added in three, 33.3 g, staged additions over a 1.5 hour period. After 21 hours at 70° C., the mixture was cooled, filtered and dried in an oven at 110° C. for 2 hours.

When placed onto a hotplate at 390° C., one large coal glowed after one minute and promptly self extinguished. No further thermal activity was noted.

EXAMPLE 2

Four quenches were completed of spent beds derived from the reaction of methyl chloride with silicon metal. For each quench, approximately 2400 gallons (20000 lbs) of water containing 150 lbs of calcium oxide (CaO) was stirred and heated to 70° C. by means of a steam lance. Without further external heating five, 500 lb. increments of spent bed were added over a four hour period. The mixture was stirred an additional 12 hours. A reaction exotherm, observed between the third and sixth hours, generated sufficient heat to raise the temperature 10°–15° C. Temperature, hydrolyzable chloride, and pH were monitored every hour. Hydrolyzable chloride is believed to be a measure of digestion and quenching efficiency. Changes in hydrolyzable chloride, pH and temperature all tended to level out by the sixth hour.

The quenched spent bed was filtered with a plate and frame filter and allowed to age outside in 2500 lb storage piles. As with other forms of spontaneous combustion, a critical mass of material, acting as a thermal insulator, is required for heat buildup until an autoignition temperature is reached. Previous experience indicates that spent bed piles of such size are sufficiently large to undergo spontaneous combustion if the spent bed is unquenched or poorly quenched. Previous experience with unquenched or poorly quenched materials has shown it would not be unusual to find pockets of silicon at 500° C. or higher in piles of this size. No fires or hot spots were observed in the piles of spent bed quenched as described in this example. In addition, the maximum temperature in each pile was monitored until the temperature had peaked and started to subside. The results are presented in Table 1.

TABLE 1

Maximum Observed Temperature in Storage Piles of Quenched Spent Bed

| Days | Pile 1 | Pile 2 | Pile 3 | Pile 4 |
|---|---|---|---|---|
| 0 | —[a] | 39 | 52 | 39 |
| 1 | 79 | — | 44 | — |
| 2 | 75 | 62 | — | — |
| 3 | 72 | 66 | — | — |
| 7 | 63 | 60 | 40 | 33 |
| 13 | — | — | — | 23 |
| 14 | — | — | 24 | — |
| 15 | — | 30 | — | — |
| 16 | 38 | — | — | — |

[a] Not measured at indicated time

EXAMPLE 3

Experiments were conducted to evaluate the effect of temperature and base strength on the quenching of a spent bed. The spent bed employed for these experiments was from the reaction of methyl chloride with silicon metal. Aqueous basic solutions of a weak basic material, $NaHCO_4$ (pH 8.6) and a strong basic material, CaO (pH 12.4) were tested. A total of 21,000 lbs (25,200 gal) of water was employed for each test. Temperatures were varied between 60° C. and 78° C. In previous experiments it was observed that the quenching reaction underwent a latent period followed by an exothermic reaction. For this series of experiments, time to initiation of the exothermic reaction was used as an indication of the relative effectiveness of quenching. Additional experimental parameters as well as the results of these experiments are presented in Table 2. The heading "Base Type" refers to the basic material used to form the aqueous basic solution. "L" denotes lime, CaO, and "B" denotes sodium bicarbonate, $NaHCO_4$. The heading "Base Amt." refers to the number of pounds of basic material added to 21,000 lb of water. The term "Spent Bed Amt." refers to the amount, in pounds, of spent bed material added to the quench reaction. The term "Exotherm Time" refers to the elapsed time until a measurable rise above the "Initial Temp." occurred.

TABLE 2

Effects of Temperature and Strength of Base on Quenching

| test # | Base Type | Amt. | Initial Temp. °C. | Spent Bed Amt. | Exotherm Time (Hrs.) |
|---|---|---|---|---|---|
| 1 | L | 150 | 60 | 2500 | 3.5 |
| 2 | L | 150 | 64 | 2500 | 3.0 |
| 3 | L | 150 | 68 | 2500 | 3.0 |
| 4 | L | 150 | 69 | 2500 | 1.8 |
| 5 | L | 150 | 69 | 2000 | 1.6 |
| 6 | L | 150 | 70 | 2500 | 3.0 |
| 7 | L | 150 | 75 | 2500 | 3.0 |
| 8 | L | 150 | 76 | 2500 | 2.0 |
| 9 | L | 150 | 78 | 2500 | 2.0 |
| 10 | L | 200 | 60 | 2500 | 2.8 |
| 11 | L | 200 | 70 | 2500 | 1.8 |
| 12 | B | 200 | 60 | 2500 | —[a] |
| 13 | B | 200 | 63 | 2500 | — |
| 14 | B | 200 | 70 | 2500 | — |
| 15 | B | 200 | 70 | 2500 | 5.3 |
| 16 | B | 200 | 78 | 2500 | 1.0 |

[a] No exothermic reaction occurred

The data demonstrates the chemical effectiveness of a strong base, CaO, in more rapidly reacting with and quenching a spent bed material at temperatures between 60°-7020 C. By contrast, the weaker basic material, $NaHCO_4$ is less effective.

What is claimed is:

1. A method of quenching a spent bed resulting from the reaction of metallic silicon with an organic halide, the method comprising:
   (A) forming an aqueous basic solution with a pH of about 10.0 to 14.0;
   (B) heating the aqueous basic solution to a temperature of about 50° C. to 100° C.;
   (C) combining the aqueous basic solution with a spent bed at a ratio in a range of about 2:1 to 5:1 to form a suspension;
   (D) stirring the suspension to effect quenching of the spent bed; and
   (E) separating the quenched spent bed from the heated aqueous basic solution.

2. The method of claim 1, where the aqueous basic solution is formed from a base selected from the group consisting of CaO, KOH, $Ca(OH)_2$, NaOH, $Na_2CO_3$, and $Mg(OH)_2$.

3. The method of claim 2, where the aqueous basic solution is heated to a temperature of about 50° to 70° C.

4. The method of claim 3, where the ratio of the heated aqueous basic solution to the added spent bed is 5:1, weight/weight.

5. The method of claim 3, where stirring the suspension to effect quenching of the spent bed is conducted for 6 to 12 hours.

6. The method of claim 5, where the aqueous basic solution contains a stoichiometric excess of cation sufficient to neutralize halogen contained in the spent bed.

7. The method of claim 6, where the aqueous basic solution is a solution of CaO.

8. The method of claim 7, where the spent bed results from a process for production of dimethyldichlorosilane.

9. The method of claim 1, where the organic halide is methylchloride; the aqueous basic solution is formed from CaO and has a pH of about 12-13; the aqueous basic solution is heated to 50°-70° C.; a final ratio of 5:1, weight/weight, of the aqueous basic solution to the spent bed is maintained; and the suspension is stirred for a period of 6-12 hours.

* * * * *